(12) United States Patent
Khanuja et al.

(10) Patent No.: US 6,979,471 B1
(45) Date of Patent: Dec. 27, 2005

(54) **COMPOSITION COMPRISING PHARMACEUTICAL/NUTRACEUTICAL AGENT AND A BIO-ENHANCER OBTAINED FROM *GLYCYRRHIZA GLABRA***

(75) Inventors: Suman Preet Singh Khanuja, Lucknow (IN); Sushil Kumar, Lucknow (IN); Jai Shankar Arya, Lucknow (IN); Ajit Kumar Shasany, Lucknow (IN); Monika Singh, Lucknow (IN); Soumya Awasthi, Lucknow (IN); Subhas Chandra Gupta, Lucknow (IN); Mahendra Pandurang Darokar, Lucknow (IN); Laiq Ur Rahman, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/655,710

(22) Filed: Sep. 5, 2000

(51) Int. Cl.⁷ .............................................. A61K 35/78
(52) U.S. Cl. ...................................... 424/757; 514/254
(58) Field of Search ......................... 424/757; 514/254

(56) References Cited

U.S. PATENT DOCUMENTS 5,478,829 A * 12/1995 Conrath
5,770,217 A * 6/1998 Kutilek, III et al.
5,939,050 A * 8/1999 Iyer et al.

OTHER PUBLICATIONS

The Merck Index Budavari et al. (eds) (1989), 11th edition, Merck & CO., Inc: New Jersey, entry Nos. 2315, 6273, and 6617.*
Registry entry for RN 1405-86-3, 2004.*
Takino et al. Planta Medica (1979), vol. 36, No. 1, pp. 74-78.*

* cited by examiner

*Primary Examiner*—Susan D. Coe
(74) *Attorney, Agent, or Firm*—Foley & Lardner LLP (57) ABSTRACT

The invention relates to a new use of a non-alkaloid compound that is plant derived glycoside 'glycyrrhizin' as a highly potent bio-enhancer of activity and availability of antibiotics and other drugs including anti-infective and anticancer agents. The molecule of invention facilitates the absorption/uptake of antibiotics and other molecules across the cell membrane in plant and animal cells as well as Gram-positive and Gram-negative bacteria and therefore can be used as a drug facilitator or bioenhancer molecule to increase the affectivity of drugs and nutraceutical agents. The compound having no antimicrobial or cytotoxic activity of its own, is a safe candidate to reduce the drug dosage towards circumventing the problem of drug resistance and the other side effects in anti-infective and anti-cancer therapies.

5 Claims, 2 Drawing Sheets

COMPOSITION COMPRISING PHARMACEUTICAL/NUTRACEUTICAL AGENT AND A BIO-ENHANCER OBTAINED FROM *GLYCYRRHIZA GLABRA*

FIELD OF THE INVENTION

The invention provides novel compositions containing extracts and compounds obtained from the plant *Glycyrrhiza glabra*, useful as bio-enhancers and bioavailability facilitators for a variety of molecules including anti-infective, anti-cancer agents and nutritional compositions. This invention also relates to a method for enhancing the biological availability, proficiency and effectivity of drugs, pharmaceuticals, nutraceuticals and other related compounds including amino acids, vitamins and other nutritional elements and ions. The present invention has direct implication in drastically reducing the dosage of antibiotics, drugs and anti-cancer agents while increasing the efficiency of absorption of nutritional elements.

BACKGROUND OF THE INVENTION

Since the invention of penicillin in 1928 by Alexander Flemming and their wider availability in the 1940s, further variants of existing and new antibiotics have been on the trial. Compared to the situation in 1954 when two million pounds of antibiotics were produced in the US, the present figure exceeds 50 million pounds. Antibiotics work either by killing bacteria (bacteriocidal) or by inhibiting growth (bacteriostatic) and their bioactivities have transformed human ability to treat many infectious diseases that previously were considered certain killers. It is estimated that globally humans consume above 250 million doses of antibiotics annually and 20%–50% of that use is unnecessary depending on the class of antibiotic. Further, widespread use of antibiotics promotes spread of antibiotic resistance many a times leading to multiple drug resistance. The total amount of antibiotic in the given dosage used for treatment of an infection generally is much higher than what is actually required to control a given population of parasite in the infected individual. This is so because all antibiotic given to the patient in a therapy does not reach the target site. This may be due to (i) lower absorption in the gut membrane when taken orally (ii) restrictive uptake by the target microbe or (iii) operation of efflux pump leading to indiscriminate extrusion of the antibiotics or therapeutic molecules. Thus, large portions of the drugs we apply are wasted and only a miniscule percentage is being targeted to the infective microbes. But even worse part is that the unutilized drug/antibiotic amount remains as a load in the body and environment. This then acts as a selection pressure, facilitating emergence of drug resistance in parasites leading to their predominance in the niche and ultimately resulting into failure of antibiotics against resistant infections. Additionally, such a situation leads to side effects, illness and reduction in life expectancy being more acute in the older population. One of the ways that has been feasible to reduce drug dosage is the occurrence of synergism between different therapeutic agents. However, even in such a situation if both the molecules have the antibiotic property, the problem of continued selection pressure on microbes is still likely to continue. Therefore, the need is for molecules, which by themselves are not microbicidal but when present with a drug or active molecule, enhance its activity and availability (bioenhancers). These molecules by their presence will not exert any selection pressure for the mutants to emerge resistant against them and on the other hand could reduce the dosage of antibiotics or drugs so that their ill effects are minimized. This way resistance development process will be substantially delayed ultimately leading to enhanced life-span of the novel and existing antibiotics. Such drug/molecule facilitators should have novel properties like non-toxic to humans, animals or plants, should be effective at a very low concentration in a combination, should be easy to formulate and most importantly enhance uptake/absorption and activity of the drug molecules. This can lead to development of judicious and strategic concentrations of antibiotics with specific bioenhancers to improve availability of the drug right up to the target for effectively controlling the infectious organisms.

The present invention was the result of planned experiments to provide a novel method for improving activity and bioavailability of antibiotics, drugs and other molecules using a plant glycoside "Glycyrrhizin" in different formulations.

The bioavailability of nutrients and enhancement of antibiotics/drugs effectivity is relevant to human, plant as well as animal health and thus the compositions and methods of the invention are also intended to be used in agriculture and veterinary practice.

DESCRIPTION OF RELATED ART

Use of ayurvedic preparation "trikatu" dates back to the period between the seventh century B.C. and the sixth century A.D., which is a Sanskrit word meaning three acrids. It refers to a combination of three elements namely, black pepper (*Piper nigrum* Linn.), long pepper (*Piper longum* Linn.) and ginger (*Zingiber officinale* Rosc.). It is believed that the use of "trikatu", and its constituents individually as well as collectively, enhances the bioavailability of a number of drugs. In specific studies carried out on animals as well as human volunteers, it was noted that the active component responsible for the increase in bioavailability of various drugs was piperine (U.S. Pat. No. 5,616,593 and 5,972,382). Till today, thus, the known documented bio-availability enhancer is piperine and a series of inventions related to this compound have been described by several prior art investigators. Though the compound piperine has been reported to be enhancing the bioavailability of drugs, nutrients and vitamins, still a proper formulation for the combination is yet to come to the market. Beside this, the compound piperine being an alkaloid would find restricted use for the reasons of its typical action.

The Applicants sought to provide a non-alkaloid molecule capable of bio-enhancing the availability of anti-infective, nutritional and anti-cancer compounds like 'taxol' produced by the yew tree in microscopic amounts.

The Applicants screened a large number of the available extracts and known compounds in the laboratory at the Central Institute of Medicinal & Aromatic Plants, Lucknow, U.P., India (CIMAP), particularly those, which by themselves did not exhibit any antibacterial property. After extensive experimentation, it was found that out of 70 pure compounds tested, only one plant compound 'glycyrrhizin', a glycoside enhanced the killing activities of different antibiotics on three diverse kinds of bacteria including *Escherichia coli*, *Bacillus subtilis* and *Mycobacterium smegmatis*. The compound is generally isolated from the roots and stolon of the plant *Glycyrrhiza glabra* and is a known sweetener and hepatoprotective drug.

Licorice (the extract from the root of the plant) is used to flavor foods, tobacco, drinks, medicines and sweets. It has expectorant action to treat bronchitis and can reduce inflammation, allergies, asthma, gastritis, peptic ulcers, rheumatism, and sore throat. It helps the liver to detoxify drugs and is used for treatment of liver disease. Licorice strengthens the immune system, stimulates the adrenal gland, and is diuretic and laxative. Licorice from roots of *Glycyrrhiza glabra*, contains glycyrrhizin, which is 50 times sweeter than sugar. Primary uses for licorice include treatment for peptic ulcers and stomach ailments, respiratory and intestinal passages. Licorice makes a wonderful expectorant expelling mucus from the chest area.

The compound when studied by the Applicants also showed enhancement in the activity of known azole class antifungal agents like clotrimazole against infectious fungal strain of *Candida albicans*. More important was the obvious enhancement in the cell division inhibitory activity against the breast cancer cell line MCF-7.

Accordingly, the Applicants have sought to increase the absorption of anti-infective, nutritional and anti-cancer compounds by the body and increase their utilization by the body by providing novel compositions containing extracts from the plant glycyrrhiza glabra.

OBJECTS OF THE INVENTION

The main object of the invention is to provide novel compositions comprising extracts and compounds from the plant *Glycyrrhiza glabra* useful as a bioenhancer and capable of improving or enhancing the bio-availability of drugs such as antibiotics, anti-infective agents and of nutritional compounds.

Another object of the invention is to provide compositions comprising extracts and compounds from the plant *Glycyrrhiza glabra* useful as bio-enhancers and bioavailability facilitators, thus enabling effective transport of drugs and molecules across biological membranes to reach target sites.

Still another object is to provide methods for enhancing the bio-availability of drugs molecules and nutritional to the target site in the body.

SUMMARY OF THE INVENTION

Accordingly, the invention provides novel compositions containing extracts and compounds from the plant *Glycyrrhiza glabra* useful as bio-enhancers and bio-availability facilitators for drugs and molecules such as antibiotics, anti-infective agents, anti-cancer agents and for nutritional compounds. The invention also provides methods for enhancing the availability of drugs, molecules and nutritional compounds to effectively reach the target site in the body.

DETAILED DESCRIPTION

Accordingly, the invention provides a composition comprising an effective amount of an extract or compound obtained from the plant *Glycyrrhiza glabra* and useful as a bio-enhancer and bioavailability facilitator together with a therapeutically effective amount of one or more nutraceuticals, antibiotics, anti-infective agents and anti-cancer agents.

In an embodiment, the composition contains an extract from the leaves, stem, roots or stolon of *Glycyrrhiza glabra*, glycyrrhizic acid or glycyrrhizin, or a combination thereof.

In still another embodiment, glycyrrhizin and glycyrrhizic acid are obtained from the plant *Glycyrrhiza glabra*.

In yet another embodiment, the anti-infective agents are selected from anti-bacterial, anti-fungal and anti-tuberculosis agents.

In yet another embodiment, the extract from the roots of *Glycyrrhiza glabra* is licorice. In an embodiment, the compound as bioavailability enhancer facilitates the transport of the compound(s) across the biological membranes to reach the target site for better effectivity/activity.

In an embodiment, the concentration of glycyrrhizin ranges from 0.05 to 50% of the weight of the anti-bacterial compounds.

In still another embodiment, the concentration of glycyrrhizin ranges from 0.10 to 10% of the weight of the nutraceutical compounds.

In yet another embodiment, the concentration of glycyrrhizin ranges from 0.25 to 20% of the weight of the anti-fungal agents.

In another embodiment, the anti-bacterial agent is selected from the group consisting of β-lactams, macrolides, quinolones, fluoro-quinolones, aminoglycosides, glycopeptides, rifamycins, folate inhibitors, tetracyclines, anti-tuberculosis agents and other similar microbicidal compounds.

In still another embodiment, the anti-fungal agent used is selected from the group comprising of polyene, triazole, imidazole, clotrimazole and other fungicidal compounds. In still another embodiment of the present invention bioenhancer improves the uptake of anti-infectives, anticancer agents and other molecules when glycyrrhizin is provided prior to the treatment with these molecules.

In yet another embodiment of the present invention the anticancer agents include paclitxel (taxol) or other cell division inhibitors controlling the growth and multiplication of tumor/cancer cells.

In yet another embodiment of the present invention living system used is selected from bacteria, fungi or any living cells.

In yet another embodiment of the present invention the bioenhancer element is used in pure form as glycyrrhizin or as precursor/derivatives like glycyrrhizic acid.

In yet another embodiment of the present invention the bioenhancer element is administered provided as licorice in form of aqueous/alcoholic extracts, decoction or direct root flakes/chips/sticks through wetting by any means.

In yet another embodiment of the present invention a pharmaceutical composition to increase the bioactivity and bioavailability comprising of the plant compound glycyrrhizin and a bio-active chemical compound selected from the group consisting of anti-bacterial, anti-fungal, anti-cancerous and other similar compounds including nutraceuticals wherein, the glycyrrhizin concentration ranges from 0.10 to 10% of the weight of the nutraceuticals compound used.

In yet another embodiment, the anti-bacterial agent is selected from the group consisting of β-lactams, macrolides, quinolones, fluoro-quinolones, aminoglycosides, glycopeptides, rifamycins, folate inhibitors, tetracyclines, anti-tuberculosis agents and other similar microbicidal compounds wherein, the glycyrrhizin concentration ranges from 0.05 to 50% of the weight of the anti-bacterial compound used.

In yet another embodiment, the macrolides comprise erythromycin, clarithromycin, azithromycin and other similar compounds.

In yet another embodiment, the quinolones and fluoro-quinolones used are selected from the group consisting of nalidixic acid, norfloxacin, ciprofloxacin, sparfloxacin and similar other compounds.

In yet another embodiment of the present invention the aminoglycosides used are selected from the group consisting of streptomycin, gentamicin, amikacin and other similar compounds.

In yet another embodiment of the present invention the glycopeptides used are vancomycin, teicoplanin and other similar compounds.

In yet another embodiment of the present invention the rifamycins used are rifampicin and other similar compounds.

In yet another embodiment of the present invention the anti-tuberculosis agents used are isoniazid, pyrazinamide, ethambutol and other similar compounds.

In yet another embodiment of the present invention the folate inhibitors are trimethoprim, sulphonamides and other similar compounds.

In yet another embodiment, the β-Lactams comprise penicillin, flucloxacillin, cloxacukkub, methicillin, cephalosporins, carbapenenms and similar compounds.

In yet another embodiment, other similar microbicidal compounds are streptogramins and oxazolidinones.

In another embodiment the anti-fungal agent is selected from the group consisting of polyene, triazole, imidazole, clotrimazole and other fungicidal compounds wherein, the glycyrrhizin concentration ranges from 0.25 to 20% of the weight of the anti-fungal compound used.

In yet another embodiment the polyenes used are amphoterecin B, nystatin and other similar compounds.

In yet another embodiment the triazoles used are fluconazole, itraconazole and other similar compounds.

In yet another embodiment the imidazoles used are ketoconazole and other similar compounds.

In yet another embodiment other fungicidal compounds are griseofulvin and terbinafine.

In yet another embodiment, the anti-cancer agent is selected from the group consisting of Paclitaxel (Taxol), Docetaxel (Taxotere), Vinblastine (Velban), Vincristine (Oncovin), Vinorelbine (Navelbine) and other similar compounds used in cancer therapy.

In another embodiment, the levels of glycyrrhizin ranges from 10 to 10,000 folds of the weight of the anti-cancer compound used.

In another embodiment, the nutraceuticals used to increase the bio-activity and bio-availability are selected from the group consisting of vitamins, amino acids, hormones and other nutritional supplements.

In yet another embodiment, the pharmaceutical compositions comprising of the plant compound glycyrrhizin in form of liquorice/dried root with the bioactive chemical compound(s) to increase their bioactivity and bioavailability wherein, the glycyrrhizin in form of liquorice preparation or dried root is given as one gram equivalent to 40 mg of glycyrrhizin.

The invention also provides a method for enhancing the bio-availability of herbal extracts, anti-infective agents, anti-cancer and nutraceutical compounds/compositions across biological membranes in living systems; said method comprising the steps of administering to a subject in need thereof, a composition comprising an effective amount of the bioenhancer obtained from the plant *Glycyrrhiza glabra*, and any one of anti-infective agents, anti-cancer agents and nutraceutical compounds.

In an embodiment, the bio-enhancer is selected from the extract of *Glycyrrhiza glabra*, glycyrrhizin, glycyrrhizic acid obtained from *Glycyrrhiza glabra* or combinations thereof.

In yet another embodiment, administration of the composition circumvents the side effects of chemotherapy by substantially reducing the dosages of therapeutic agents comprising of anti-bacterial, anti-fungal and anti-cancerous agents wherein the side effects of those agents can be bone marrow suppression, liver and kidney toxicity, pulmonary scarring, high fevers, skin reactions, Nausea and vomiting, hair loss, skin rash, mouth sores, diarrhoea, loss of appetite and confusion, lethargy and ambulation problems (ataxia), anaphylactic reactions (consisting of fast heart rate, wheezing, lowered blood pressure and facial edema, cerebellar dysfunction (consists of slurring of speech, walking problems, as well as eye motion problems), loss of periods (menses), ovarian failure can occur, painful soft tissue ulcers, cardiotoxicity, hypersensitivity reactions, abnormal blood pressure, sweating, bleeding, shortness of breath and many related problems.

In still another embodiment, the bioenhancer improves the uptake of anti-infectives, anticancer agents and other molecules when glycyrrhizin is provided prior to the treatment with these molecules.

The invention also provides use of the extract or the compound obtained from the plant *Glycyrrhiza glabra*, as a bioenhancer and bioavailability and facilitator of nutritional compounds and drugs and molecules selected from anti-infective and anti-cancer agents.

The invention is described in detail herein below with reference to the following drawings wherein.

Figure 1:
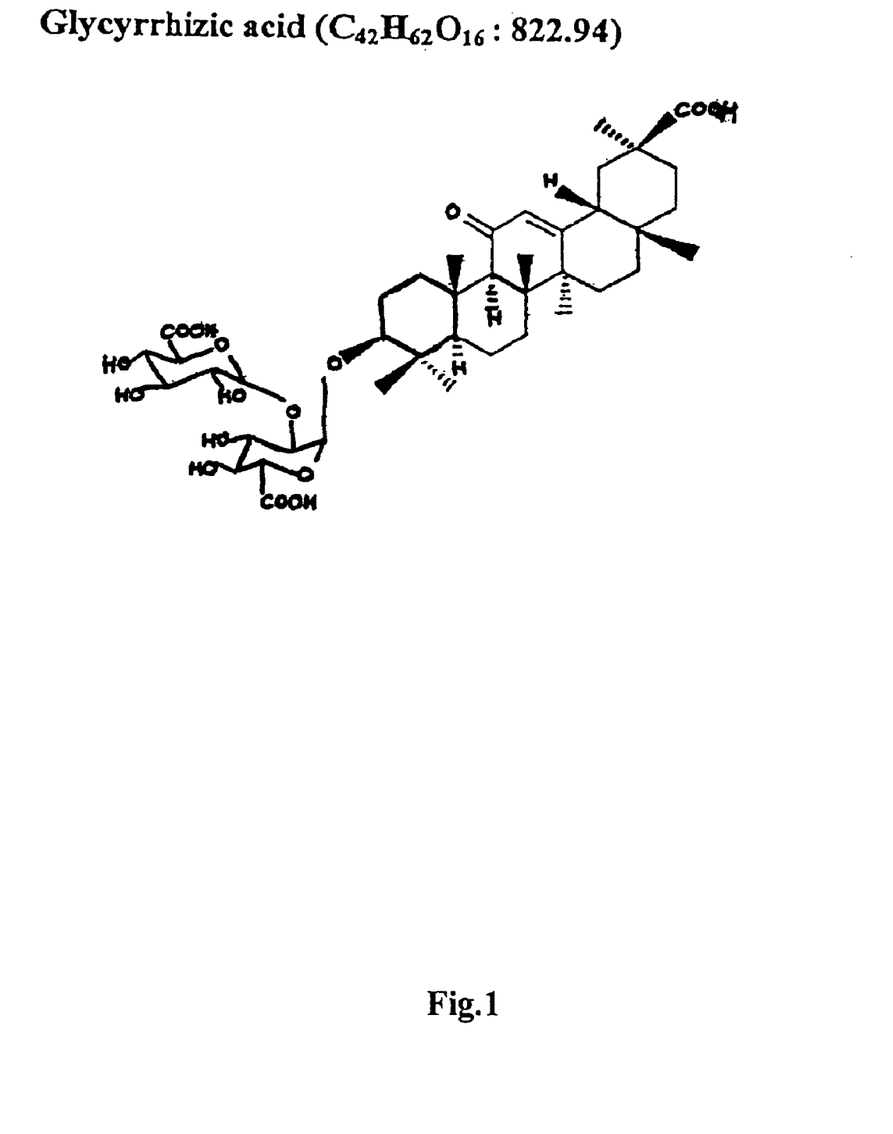
FIG. 1: represents the structural formula of Glycyrrhizic acid.
Figure 2:
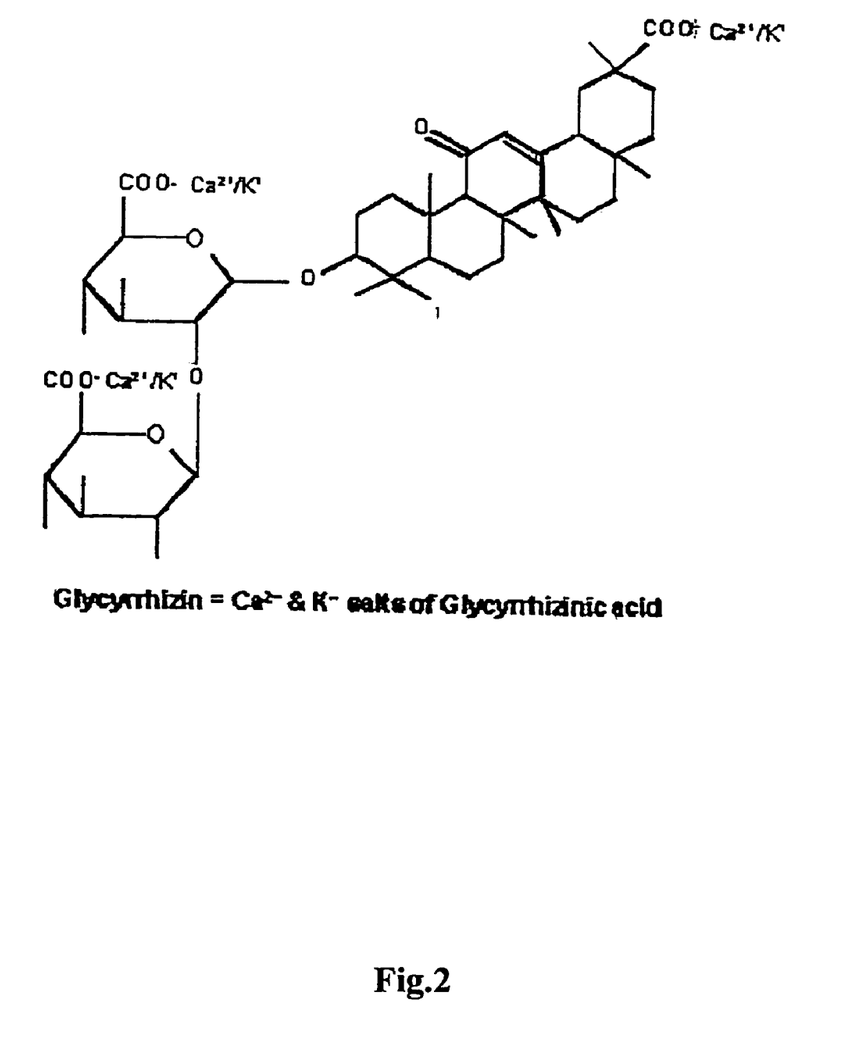
FIG. 2: represents the structural formula of Glycyrrhizin.

Some of the embodiments of the invention are illustrated herein below by the following bioassays and examples which are provided merely to illustrate the invention and should not be construed as limitations on the inventive concept embodied herein.

The methodology followed for screening of this compound (Glycyrrhizic acid and Glycyrrhizin) included specifically designed bioassays as follows:

1. Assay for Bio-Enhancement of Anti-Infective Agents a) The minimum inhibitory concentration (MIC) of any antibiotic or drug molecule is determined against *Escherichia coli* (ATCC 10536), *Bacillus subtilis* (ATCC 6015) and *Mycobacterium smegmatis* (ATCC 14468) and *Candida albicans* (ATCC 10231) in broth and disc diffusion assays.

b) The antibiotics or antifungal agents at concentrations ⅒, ⅛, ⅙, ¼, ⅓, ½ and equal to MIC are added alone and in combination with the test compound at varying concentrations in broth assays to evaluate the comparative level of inhibition and similarly at varying concentrations in disc diffusion assay.

c) The combinations showing enhancement in terms of higher activity than antibiotic alone for the inhibition of bacterial growth (large inhibition zone in disc diffusion and higher killing at lower concentration in broth assay) are picked up for future testing.

d) In broth assays the activity is quantified by counting number of viable cells in a given treatment and converted in fold enhancement by the combination treatment compared to antibiotic/drug alone in the killing percentage of cells.

e) The pretreatment assay is followed to determine whether the bioenhancer which may be either an extract obtained from the plant *Glycyrrhiza glabra*, glycyrrhizin or glycyrrhizic acid, is required along with antibiotic to enhance its activity or even its withdrawal after treatment or prior to antibiotic treatment would benefit. For this, the cells are treated with the bioenhancer/compound for 4 to 8 hours and then washed free of it by centrifugation and washing in sterile water. This is followed by treatment with antibiotic/drug as in steps (b) to (d) above.

f) The results of the bio-assays carried out are represented in the tables provided hereinbelow wherein tables 1–4 represent the activity of glycyrrhizin. Tables 7–9 depict the activity of glycyrrhizic acid and tables 10–11 depict the activity of licorice.

2. Assay for Bio-Enhancement of Anti-Cancer Agents a) MCF-7 (Breast cancer cell line is inoculated at a density of about $0.1 \times 10^6$ cells in MEM medium in the wells of 24 well plate.

b) The used up medium in these cultures is replaced with fresh medium after 18 hours in each well.

c) The test compound (s) is added at desired concentrations in different wells just after the medium replacement.

d) Observations are recorded on the cell count after 36 hours for which the following steps are required.
   i. The medium is removed from the wells.
   ii. The wells are rinsed with 1 ml PBS (Phosphate buffer saline).
   iii. To each well 500 µl of freshly prepared trypsin solution (0.1% in PBS) is added.
   iv. Trypsin solution is removed after 30 seconds and the plate is gently tapped till the cells are released from the plate surface.
   v. Fresh 1 ml of MEM growth medium is added and agitated with a pipette to obtain a cell suspension.
   vi. 10 µl of cell suspension is taken on the haemocytometer and a cover glass is placed over the counting chamber.
   vii. The number of viable cells is counted in 5 big squares and the reading is taken from 5 microscopic fields to determine the average.
   viii. The cell count (titre per ml) in the original sample is then calculated as average count$\times 10^3$.

Composition of Minimum Essential Medium (MEM): 100 ml

| | |
|---|---|
| MEM powder (Sigma-Aldrich, USA) | 0.96 g |
| HEPES Buffer (Sigma-Aldrich, USA) | 0.26 g |
| Sodium Bicarbonate | 0.22 g |
| Penicillin G | 10 mg |
| Streptomycin | 20 mg |
| Gentamycin | 5 mg |
| Foetal Calf Serum | 15 ml |
| Foetal Calf Serum | 15 ml |
| Distilled water | 85 ml |

3. Bioavailability Tests Through Biological Membrane a) A specially designed U-tubes of glass consisting of two component (opposite-L type) were used in which one open end of a L-shaped was tapered to fit within the untapered end of the other L-tube.

b) The membrane of goat gut (initial part) was stretched and fixed to act as the barrier between the two ends such that by joining the two L-tubes, a U-tube was made.

c) Sterile distilled water was then filled in both the sides to equal height/level.

d) The antibiotic/compound was added to the donor tube (tapered) and through spectro-photometer the transfer of molecule was observed using UV and visible absorption maxima of the respective molecules by taking the OD at defined wavelengths.

EXAMPLES

In the next step of elucidation of the enhancer action the applicants experimented with the killing activities of different antibiotics against the bacteria singly and in combination with the test compound glycyrrhizin following the method described above. These experiments are to be considered with assay for bioenhancement of the compounds glycyrrhizin/glycyrrhizic acid and licorice, as described earlier. When the bacteria were grown in presence of the compound as such no significant killing was observed. In all the experiments the glycyrrhizin concentration was kept at 1 µg/ml, unless it is specifically mentioned.

Example 1

Glycyrrhizin Mediated Enhancement in the Killing Action of Antibiotics Against Gram-Negative Bacterium *Escherichia coli*

TABLE 1

| Antibiotics | Concentration µg/ml | Survival fraction of viable cells upon treatment with antibiotic alone (a) | Survival fraction of viable cells upon treatment with antibiotic- glycyrrhizin combination (b) | *Folds enhancement in antibiotic activity (a/b) |
|---|---|---|---|---|
| Rifampicin | 10 | 0.42 | 0.11 | 3.8 |
| Rifampicin | 20 | 0.28 | 0.02 | 14.0 |
| Nalidixic acid | 8 | 0.19 | 0.02 | 9.5 |
| Tetracycline | 2 | 0.42 | 0.22 | 1.9 |
| Tetracycline | 4 | 0.27 | 0.03 | 9.0 |
| Ampicillin | 6 | 0.38 | 0.03 | 12.6 |
| Ampicillin | 8 | 0.013 | 0.006 | 2.1 |

Example 2

Glycyrrhizin Mediated Enhancement in the Killing Action of Antibiotics Against Gram-Positive Bacterium *Bacillus subtilis*

TABLE 2

| Antibiotics | Concentration µg/ml | Survival fraction of viable cells upon treatment with antibiotic alone (a) | Survival fraction of viable cells upon treatment with antibiotic- glycyrrhizin combination (b) | *Folds enhancement in antibiotic activity (a/b) |
|---|---|---|---|---|
| Nalidixic acid | 6 | 0.50 | 0.11 | 4.50 |
| Nalidixic acid | 8 | 0.27 | 0.04 | 6.75 |
| Tetracycline | 1 | 0.10 | 0.02 | 5.00 |

Example 3

Glycyrrhizin Mediated Enhancement in the Killing Action of Antibiotics Against Bacterium *Mycobacterium smegmatis*

TABLE 3

| Antibiotics | Concentration μg/ml | Survival fraction of viable cells upon treatment with antibiotic alone (a) | Survival fraction of viable cells upon treatment with antibiotic-glycyrrhizin combination (b) | *Folds enhancement in antibiotic activity (a/b) |
|---|---|---|---|---|
| Rifampicin | 0.5 | $0.56 \times 10^{-4}$ | $0.086 \times 10^{-4}$ | 6.5 |
| Nalidixic acid | 4 | 0.70 | 0.12 | 7.7 |
| Tetracycline | 0.5 | 0.3 | 0.2 | 1.5 |

From the above experiments it was deduced that the potency of the antibiotic is increased when applied along with the compound glycyrrhizin. It was interesting to note that the same results were observed when the bacterial cells were pretreated with glycyrrhizin for 4–8 hours and then the cells were washed free of the glycyrrhizin by centrifugation and resuspending the cells in fresh medium followed by treatment with respective antibiotics. This implicated some changes induced by glycyrrhizin on the bacterial surface/membrane making it more receptive to the antibiotics and hence enhancing bioavailability and ultimately activity/bactericidal effect of the given antibiotic.

Example 4

Glycyrrhizin Mediated Enhancement Observed in Disc Diffusion Assays for the Killing Action of Antifungal Agent Against *Candida albicans*.

TABLE 4

| Clotrimazole (μg/disc) | Glycyrrhizin (μg/disc) | Zone of inhibition (mm) |
|---|---|---|
| 0 | 0 | 0 |
| 0 | 1 | 0 |
| 4 | 0 | 7 |
| 4 | 1 | 11 |

Example 5

Glycyrrhizin Mediated Enhancement in the Activity of Anticancerous Agent "Taxol"

TABLE 5

| Taxol Concentration (μg/ml) | Initial titre of viable cells | Final titre of viable cells upon treatment with taxol alone | Final titre of viable cells upon treatment with taxol-glycyrrhizin combination |
|---|---|---|---|
| 0.01 | $0.1 \times 10^6$ | $0.05 \times 10^{-6}$ | $0.025 \times 10^6$ |
| 0.02 | $0.1 \times 10^6$ | $0.04 \times 10^{-6}$ | $0.024 \times 10^6$ |
| 0.05 | $0.1 \times 10^6$ | $0.03 \times 10^{-6}$ | $0.021 \times 10^6$ |
| Without taxol | | Final titre | |
| Control | $0.1 \times 10^{-6}$ | $0.16 \times 10^{-6}$ | |
| Control (glycyrrhizin) | $0.1 \times 10^{-6}$ | $0.12 \times 10^{-6}$ | |

Example 6

Glycyrrhizin Mediated Enhancement in the Bioavailability Across the Biological Membrane

TABLE 6

| Compound(s) in the donor tube | length (nm) | OD measured as Absorbance (specific to the compound maxima) across the membrane in receiving tube after | | | | | |
|---|---|---|---|---|---|---|---|
| | | 1 hr | 2 hr | 3 hr | 4 hr | 5 hr | 6 hr |
| Rifampicin | $A_{340}$ | 0.0039 | 0.0275 | 0.0371 | 0.0440 | 0.0906 | 0.1165 |
| | $A_{475}$ | 0.0015 | 0.0148 | 0.0210 | 0.0297 | 0.0334 | 0.0394 |
| Rifampicin + Glycyrrhizin | $A_{340}$ | 0.0070 | 0.0638 | 0.1465 | 0.2090 | 0.3424 | 0.3930 |
| | $A_{475}$ | 0.0100 | 0.0395 | 0.0575 | 0.1362 | 0.2365 | 0.2853 |
| Vitamin B-12 | $A_{360}$ | 0.0250 | 0.0556 | 0.0714 | 0.1283 | 0.1370 | 0.1595 |
| | $A_{530}$ | | | | | | |
| Vitamin B-12 + Glycyrrhizin | $A_{360}$ | 0.0582 | 0.0627 | 0.1058 | 0.2051 | 0.2616 | 0.2984 |
| | $A_{530}$ | | | | | | |

Here, the applicants observed glycyrrhizin-mediated enhancement in the cell division inhibitory action of anticancer agent taxol in the animal cell culture experiments using cancerous cell line MCF-7. As evident in Table 5 above, the anticancerous activity of 'Taxol' in terms of inhibiting the growth and multiplication of MCF-7 cancer cells was markedly enhanced by at least 5 folds. In these experiments, the cancerous cells growth inhibition by Taxol (@ 0.01 $\mu$g/ml) in presence of glycyrrhizin (@ 1 $\mu$g/ml) was higher than even the treatment with taxol (@ 0.05 $\mu$g/ml) alone.

Example 7

Glycyrrhizic Acid Mediated Enhancement in the Killing Action of Antibiotics Against *Escherichia coli* in Broth Assay.

TABLE 7

| Antibiotics | Concentration $\mu$g/ml | Survival fraction of viable cells upon treatment with antibiotic alone (a) | Survival fraction of viable cells upon treatment with antibiotic glycyrrhizic acid combination (b) | *Folds enhancement in antibiotic activity (a/b) |
|---|---|---|---|---|
| Rifampicin | 20 | 0.57 | 0.281 | 2.03 |

TABLE 8

Glycyrrhizic acid mediated enhancement in the killing action of antibiotics against *Escherichia coli* in disc diffusion assay.

| Rifampicin ($\mu$g/disc) | Glycyrrhizic acid ($\mu$g/disc) | Net zone of inhibition (mm) |
|---|---|---|
| 0 | 0 | 0 |
| 0 | 4 | 0 |
| 500 | 0 | 2 |
| 500 | 4 | 3 |

TABLE 9

Glycyrrhizic acid mediated enhancement in the killing action of antibiotics against *Mycobacterium smegmatis* in disc diffusion assay.

| Rifampicin ($\mu$g/disc) | Glycyrrhizic acid ($\mu$g/disc) | Net zone of inhibition (mm) |
|---|---|---|
| 0 | 0 | 0 |
| 0 | 4 | 0 |
| 0.4 | 0 | 3 |
| 0.4 | 4 | 4 |

In the above experiments, the Applicants used Glycyrrhizic acid to test the potency of this acid in enhancing the activity of antibiotics. The Applicants observed that the killing action the antibiotics (such as Rifampicin) is enhanced when used with *Glycyrrhizic* acid. Table 7 shows that when the cells were treated with Rifampicin alone, the survival fraction was about 0.57. However, the survival fraction of cells when treated with a combination of rifampicin and glycyrrhizic acid was much less i.e. about 0.281. This shows that the combination of glycyrrhizic acid with rifampicin enhances the availability of rifampicin to the cells. Similarly, the results of the disc diffusion assay also show that the combination of glycyrrhizic acid with rifampicin is more effective against mycobacterium smegmatis than glycyrrhizic acid or rifampicin used singly.

Example 8

Licorice (25 ($\mu$g/ml) Mediated Enhancement in the Killing Action of Rifampicin Against Gram-Negative Bacterium *Escherichia coli*.

TABLE 10

| Antibiotics | Concentration $\mu$g/ml | Survival fraction of viable cells upon treatment with antibiotic alone (a) | Survival fraction of viable cells upon treatment with antibiotic glycyrrhizic acid combination (b) | *Folds enhancement in antibiotic activity (a/b) |
|---|---|---|---|---|
| Rifampicin | 10 | 0.420 | 0.135 | 3.10 |

TABLE 11

Licorice (25 $\mu$g/ml) mediated enhancement in the killing action of antibiotics against Gram-positive bacterium *Bacillus subtilus*.

| Antibiotics | Concentration $\mu$g/ml | Survival fraction of viable cells upon treatment with antibiotic alone (a) | Survival fraction of viable cells upon treatment with antibiotic glycyrrhizic acid combination (b) | *Folds enhancement in antibiotic activity (a/b) |
|---|---|---|---|---|
| Nalidixic acid | 6 | 0.500 | 0.121 | 4.10 |

Tables 10 and 11 show the bio-enhancing effects observed in the use of licorice, the extract from the roots of *Glycyrrhiza glabra*. As can be seen from Tables 10, the survival rate of bacteria treated with the antibiotic Rifampicin is more than when treated with a combination of Rifampicin and licorice. Similarly, Table 11 shows that the survival rate of the bacteria treated with nalidixic acid is less than when treated with a combination of nalidixic acid and licorice. The results in Tables 10 and 11 demonstrate the use of licorice as an effective bio-enhancer and bioavailability facilitator.

In the experiments related to transport across the mammalian gut membrane, it was observed that the compound glycyrrhizin enhances the transport of antibiotics e.g. Rifampicin, Tetracycline, Nalidixic acid, Ampicillin and vitamins like B-1 and B-12 across the gut as well as artificial membrane. The enhancement in transport is approximately 2 to 6 folds.

Several medicinal plants are cited for use in Indian system of medicine for various activities such as immunostimulant, adaptogenic, anticancer, antimalarial, antimicrobial, angiogenetic, hepatoprotective, hypolinidemic, hypoglycemic, memory enhancing etc. The genus *Glycyrrhiza* (Mulethi) has attracted sizable importance for compound(s) with hepatoprotective ability. In *Glycyrrhiza glabra* (family, Leguminosae) 12 different varieties (Biovars) are known. Among these only three namely *typica, glandilifera* and *violacea* are commonly used for the pharmaceutical and confectionary requirements. *Glycyrrhiza glabra* var. *typica* is the source of Spanish Liquorice and is sweeter than other types. *Glycyrrhiza glabra* var. *glandilifera* is the source of Russian liquorice, which is moderately sweet and some what bitter, also more or less acrid. *Glycyrrhiza glabra* var. *violacea* is known as the Persian or Iranian liquorice of commerce and has thick roots. The name *Glycyrrhiza* (popularly known as mulethi in India) is of Greek origin meaning sweet root. Cultivation of this species is mostly limited to US, Eastern Europe and several CIS of former USSR and scattered in western and northern India. The roots of the plant *Glycyrrhiza glabra* are highly useful as these contain the important glycoside Glycyrrhizin for its hepatoprotective ability. The root extracts also contain flavonoids, saponins, sterols, amino acids, gums essential oils, sugars and starches. The plant takes at least 4–5 years to achieve substantial production of glycyrrhizin in the roots. Generating sufficient planting material for commercial cultivation is thus desirable for harvesting required quantity of Glycyrrhizin on sustainable basis.

This molecule (Glycyrrhizin) is a known sweetener and hepatoprotective drug. It helps the liver to detoxify drugs and is given for liver disease. The molecule is known to be strengthening the immune system, stimulates the adrenal gland, and is diuretic and laxative. This is also used to treat peptic ulcers and stomach ailments, respiratory and intestinal passages. Considering the wide use of the molecule in traditional system of medicine and the level of toxicity well tested, this can be used along with the antibiotics and other molecule of importance to enhance the efficacy on the target. This molecule (glycyrrhizin) in the Applicant's study facilitates the transport/uptake of various compounds including antibiotics, antifungal and anticancer agents, vitamins and amino acids etc. across the membrane thereby increasing the absorption or bioavailability various biological systems including bacteria, animal and plant cells. This thus has immense importance for absorption of the drugs, pharmaceuticals, nutraceutical and other related compounds and ions by the cells and hence huge potential of being used as drug/molecule facilitators.

Great emphasis now is being laid towards quality assurance of crude drugs from plants sources widely used in the Indian system of medicine. The scientific study of traditional medicines, derivation of drugs through bioprospection and systematic conservation, domestication and cultivation of the concerned medicinal plants has assumed great importance in the present day context when more and more people prefer safe and effective medicines at affordable price for curing their ailments. The present invention enlarges the scope and use of the natural glycoside glycyrrhizin in therapeutical and nutraceutical application. These plants synthesizing multi-use molecules are *Glycyrrhiza* sps and *Abarus* sps. The preferred plant is *Glycyrrhiza glabra* which is propagated through underground rhizome. This demands large amount of planting material which may be possible by micro propagation in vitro for its commercial cultivation. Agrotechnology and suitable cultivars for its cultivation in India are therefore required through screening of germplasm and genetic selection. At CIMAP a genetically superior variety of *Glycyrrhiza glabra* var. *typica* named as 'Misree' is available for cultivation with better yield of glycyrrhizin (Kukreja A K, Tyagi B R, Muni Ram and Sushil Kumar (1997) Liquorice cultivar—Mishree. *Journal of Medicinal and Aromatic Plants Sciences.* 19: 732–733). Procedure for isolation of quality glycyrrhizin the main compound from the root extract. Of the plant *Glycyrrhiza glabra* var. *typica* was also standardized. For this purpose we choose the plant *Glycyrrhiza glabra* var. *typica* 'Misree' (the released variety of CIMF) and commercially available plant material. Fresh roots were harvested from the plant and shade dried. Commercial dried roots were purchased from the market. The protocol followed for the isolation was as follows:

Protocol:
1. Plant material (250 gram) was dipped in 900 ml of Butanol: glacial acetic acid ethyl alcohol (1:1:1) for 48 hours.
2. This was filtered through filter paper and concentrated in vacuums rota-vapour.
3. The solid material thus obtained was dissolved in acetic acid (180 ml) and treated with diethyl ether 2 liter (10 times, each with 200 ml) to remove impurity as precipitate which was filtered out.
4. Then the liquor in diethyl ether was evaporated to 250 ml and fractionated through liquid—liquid fractionation twice in water, followed by discarding the water fraction.
5. This diethyl ether fraction was further concentrated in vacuum rotavapour to obtain the compound.
6. The compound was hydrolyzed with 80 ml of NaOH (NaOH 5% in Methaol) at 80°–90° C. for 1 hour.
7. The hydrolyzed reaction mixture was acidified (100 ml of glacial acetic acid acetic acid and 5 ml of concentrated HCl) to pH 3.6 to form a ppt which was filtered and washed with ethanol.

After isolation, the compound was checked for the purity compared to the standard glycyrrhizin obtained from Sigma chemical Inc. Preparation of the test solution: One gram of the isolated compound was extracted in 20 ml chloroform for 15 min. After filtration the filtrate was discarded. The marc was refluxed for 1 hour with 30 ml of 0.5 M $H_2SO_4$. The unfiltered mixture was then cooled and extracted with chloroform (2×20 ml) and the combined $CHCl_3$ extract was concentrated. The residue was dissolved in 1.0 ml $CHCl_3$: Methanol (1:1) mixture.

Reference solution: Five milligram of glycyrrhizin was refluxed with 20 ml 0.5 M $H_2SO_4$. This was cooled and extracted with chloroform (2×10 ml). The combined $CHCl_3$ extract was evaporated and the residue was dissolved in 1.0 ml $CHCl_3$: Methanol (1:1) mixture.

Solvent system: Toluene: ethyl acetate: glacial acetic acid (12.5: 7.5:0.5).

Procedure: The test and reference solutions were applied in two different tracks on a precoated silica gel $GF_{254}$ plate (5×15 cm) of uniform thickness (0.2 mm). The plate was developed in the solvent system to a distance of 12 cm.

Scanning: The plate was scanned densitometrically at 254 nm in both the tracks and the fingerprint profiles were recorded.

Visualization of spots:
(i) Under UV 254 nm.
(ii) The plate was sprayed with anisaldehyde-sulfuric acid reagent and heated at 110° C. for 5–10 min.

Evaluation:
(i) Under UV 254 nm light (before spraying):one spot (0.41) was visible in the sample solution track, corresponding to (Rf 0.41) glycyrrhetic acid of reference track.
(ii) In daylight (after spraying): Gylcyrrhetic acid was visible as a dark violet spot in both reference and test solution tracks.

The above experiments indicate a sound procedure of isolating fairly pure glycyrrhizin from the root of the plant variety 'Misree' of CIMAP as well as market available dry root samples. By this procedure about 0.1 to 0.25% of glycyrrhizin could be isolated. The protocol can be scaled up or scaled down depending upon the initial starting material.

Advantages.

1. The plant extract of *Glycyrrhiza glabra* and glycyrrhizin in the Applicant's study facilitates the transport/uptake of various compounds including antibiotics, antifungal and anticancer agents, vitamins and amino acids etc. across the membrane thereby increasing the absorption or bioavailability various biological systems including bacteria, animal and plant cells. This thus has immense importance for absorption of the drugs, pharmaceuticals, nutraceutical and other related compounds and ions by the cells and hence huge potential of being used as drug/molecule facilitators.
2. The present invention enlarges the scope and use of the natural glycoside glycyrrhizin in therapeutical and nutraceutical application.
3. Glycyrrhizin is nontoxic to humans, animals or plants, is effective at very low concentrations in a combination, easy to formulate and enhances the uptake/absorption and activity of drug molecules. Thus the novel use of this compound as described in the present invention is safe and effective for bioenhancement of activity of drugs.
4. Glycyrrhizin by its presence will not exert any selection pressure for the mutants to emerge resistant against them and reduce the dosage of antibiotics or drugs so that their ill effects are reduced.

What is claimed is:

1. A composition comprising (i) a bioenhancer or bioavailability facilitator selected from the group consisting of isolated and purified Glycyrrhizic acid, isolated and purified Glycyrrhizin or mixtures thereof in a concentration of about 1 µg/ml and (ii) an agent selected from one or more nutraceuticals, antibiotics, anti-infective agents, and anti-cancer agents, wherein both said bioenhancer or bioavailability facilitator and said agent are present in amounts insufficient by themselves to be therapeutically effective nutraceuticals, antibiotics, anti-infective agents or anti-cancer agents.

2. A composition as claimed in claim 1, wherein the anti-infective agents are selected from anti-bacterial, anti-fungal and anti-tuberculosis agents.

3. The composition of claim 2, wherein the concentration of glycyrrhizin ranges from 0.05 to 50% of the weight of the anti-bacterial compounds.

4. A composition as claimed in claim 2 wherein the anti-bacterial agents are selected from the group comprising consisting of β-lactams, macrolides, quinolones, fluoro-quinolones, aminoglycides, glycopeptides, rifamycins, folate inhibitors, tetracyclines, anti-tuberculosis agents and microbicidal compounds.

5. A composition as claimed in claim 4 wherein the quinolones and fluoro-quinolones are selected from the group consisting of nalidixic acid, norfloxacin, ciprofloxacin and sparfloxacin.

* * * * *